United States Patent [19]

Kameswaran et al.

[11] Patent Number: 4,857,550

[45] Date of Patent: Aug. 15, 1989

[54] NOVEL INSECTICIDAL DIBENZOYL-TERT-BUTYLCARBAZONITRILE COMPOUNDS AND METHOD FOR THE PREPARATION THEREOF

[75] Inventors: Venkataraman Kameswaran, Princeton; Donald P. Wright, Jr., Pennington; Rod A. Herman, Allentown, all of N.J.

[73] Assignee: American Cyanamid Company, Stamford, Conn.

[21] Appl. No.: 237,346

[22] Filed: Aug. 29, 1988

[51] Int. Cl.[4] .................. C07C 121/60; C07C 125/08; A01N 37/34; A01N 47/40
[52] U.S. Cl. .................................... 514/522; 514/609; 558/415; 564/105
[58] Field of Search ................ 514/609, 522; 564/105; 558/415

[56] References Cited

U.S. PATENT DOCUMENTS 1,611,941 12/1926 Osborne et al. ...................... 564/105
4,206,141 6/1980 Mihailovski .................... 564/105 X Primary Examiner—Joseph Paul Brust
Attorney, Agent, or Firm—Estelle J. Tsevods

[57] ABSTRACT

The present invention provides novel insecticidal dibenzoyl-tert-butylcarbazonitrile compounds and a method for the preparation thereof. It also provides methods for controlling insects with said dibenzoyl-tert-butylcarbazonitrile compounds and for protecting growing plants, crops, trees, shrubs and ornamentals, from attack by said insects.

15 Claims, No Drawings

NOVEL INSECTICIDAL DIBENZOYL-TERT-BUTYLCARBAZONITRILE COMPOUNDS AND METHOD FOR THE PREPARATION THEREOF

BACKGROUND OF THE INVENTION

The present invention relates to novel dibenzoyl-tert-butylcarbazonitrile compounds which are highly effective for controlling insect pests and protecting growing plants, trees, shrubs and the like, from attack by such pests. The compounds of the present invention are hitherto unknown substituted and unsubstituted diacylhydrazines useful as insecticidal agents.

A variety of acylhydrazines are known. For instance, 1,2-dibenzoyl-1-alkylhydrazines are disclosed in a paper by Q. N. Porter and A. E. Seif entitled Mass Spectrometric Studies XI Skeletal Rearrangements in Acylhydrazines; published in *Aust. J. Chem.*, 1972, 25, 523–9. Similarly, 4-nitrobenzoic acid 2-benzoyl-1-(1,1-dimethylethyl)hydrazine is described by Maerky, Michael, Meir et al., in a paper entitled The Photochemistry of Sydnones and 1,3,4-oxadiazolin-2-one, *Helv. Chem Acta*, 1978, 61(4), 1477–510. Again, no utility is reported for this compound.

Although Japanese patent application JP-050819, filed 17-4-80, publication No. J5 6,147,066 describes N,N'-dibenzoyl-N,N'-dialkyl-alkylenediamines for detecting blood in body fluids, insecticidal use of the disclosed compounds is neither described nor suggested.

In a Nissan Chemicals Industry Ltd. Japanese patent application JA-091048, filed 11-9-72 publication No. J4 9,047,528, benzoylhydrazine derivatives as acaricidal agents are disclosed. This publication does not suggest or disclose benzoyl-tert-butylcarbazonitriles for control of insects. The Nippon Soda Co. Ltd Japanese patent application JA-020216, filed 18-3-69, publication No. JA 7,302,770-R, describes a number of N-substituted-N-phenylhydrazines and indicates that these compounds exhibit insecticidal and miticidal activity. The publication does not, however, describe or suggest that dibenzoyl-tert-butylcarbazonitriles are effective as insecticidal agents.

Offenlegungsschrift DE No. 3228631 describes 1-phosphorylthioacetyl-2-acyl-hydrazines as insecticidal, acaricidal, fungicidal and nematocidal agents. These compounds are only remotely related to the compounds of the present invention since they are acylhydrazines but contain a phosphate or thiophosphate function.

Although intermediates useful in the preparation of the dibenzoyl-tert-butylcarbazonitriles of the present invention are described in U.S. patent application Ser. No. 926,779 filed Nov. 12, 1986, the compounds disclosed do not, however, contain a cyano function, nor is the introduction of a cyano function obvious from, or suggested by, the above-said application. Moreover, the substituted and unsubstituted dibenzoyl-tert-butylcarbazonitriles of the present invention are unexpectedly effective as a systemic insecticidal agents against larvae and crop protection agents.

It is an object of the present invention to provide novel substituted and unsubstituted dibenzoyl-tert-butylcarbazonitrile compounds useful in controlling a wide variety of insect pests and protect growing plants, trees, shrubs and the like from attack by said pests.

It is a further object of the present invention to provide methods of preparing the compounds of the invention and methods of using said compounds as insecticidal agents. These and other objects of the present invention will become evident by the detailed description of the invention hereinbelow.

SUMMARY OF THE INVENTION

The present invention relates to novel insecticidally-effective substituted and unsubstituted dibenzoyl-tert-butylcarbazonitrile compounds having the formula I structure:

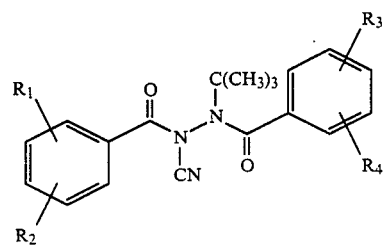

wherein $R_1$, $R_2$, $R_3$ and $R_4$ each independently represent H, F, Cl, Br, I, $CH_3$, $OCF_3$, $CF_3$, $OCHF_2$, CN or $NO_2$.

The present invention also relates to methods for protecting growing plants from insect attack by applying to the foliage of said plants or to the soil or water in which they are growing, an insecticidally effective amount of a formula (I) dibenzoyl-tert-butylcarbazonitrile.

Advantageously, it has been found that the above-said formula (I) compounds are excellent stomach poisons for insects and highly effective systemic insecticides that are taken up through the root systems of plants, thereby protecting the root systems, stems and foliage of the treated plants from the ravages of feeding insects.

When used systemically, the formula (I) substituted or unsubstituted dibenzoyl-tert-butylcarbazonitriles are applied to the soil or water in which the plants are growing, generally in the form of solid or liquid formulations which are readily dispersed and/or dissolved in the soil or water.

As highly effective stomach poisons, these compounds may also be applied as liquid sprays to the foliage and stems of the plants which are to be protected from feeding insects.

DETAILED DESCRIPTION OF THE INVENTION

Especially preferred dibenzoyl-tert-butylcarbazonitriles useful in the practice of the present invention are depicted by the formula (II) structure:

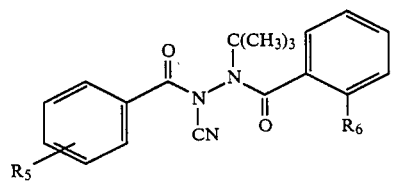

wherein $R_5$ is H, F, Cl or Br; and $R_6$ is H, F, Cl, Br, I, $CH_3$, $OCH_3$, $CF_3$, CN or $NO_2$.

The above-said formula I and formula II dibenzoyl-tert-butylcarbazonitriles are readily formulated as solid or liquid formulations. When used for the protection of living plants, they are generally applied to the foliage of said plants, or to the soil or water in which they are growing, in amounts sufficient to provide about 0.01 kg/hectare to about 8.0 kg/hectare, and preferably 0.025 kg/hectare to 4.0 kg/hectare of the formula (I) or formula (II) compound. When applied to plants in the form of a liquid spray, said spray should contain about 10 ppm to about 10,000 ppm of the active dibenzoyl-tert-butylcarbazonitrile.

Compositions

In practice, it is found that the active dibenzoyl-tert-butylcarbazonitriles of this invention are prepared as emulsifiable concentrates, wettable powders, aqueous flowables, granular formulations and the like.

A typical emulsifiable concentrate formulation is prepared by dispersing about 30% w/v of 2,3-dibenzoyl-2-tert-butylcarbazonitrile; 50% w/v of 2-pyrrolidone; in 10% w/v of n-butanol; 7% w/v of a polyalkylene glycol ether such as POLYFAR® S320 manufactured by Westvaco-Polychemicals, Charleston Heights, S.C. and 3.0% w/v of nonylphenoxy polyethoxy ethanol offered by Rohm and Haas Co as TRITON® N101.

Emulsifiable concentrates are especially useful for distributing the active dibenzoyl-tert-butylcarbazonitrile of this invention since they are readily dispersed in water for application as liquid sprays. They are added to irrigation water or flooded paddies such as used for rice cultivation or applied directly to the plants or the locus to be protected from insect infestation using aerial applicators or ground equipment.

Granular formulations are prepared by dissolving the dibenzoyl-tert-butylcarbazonitrile in a low-boiling solvent such as methylene chloride and spraying the thus prepared solution on a sorptive carrier such as kaolin, bentonite, attapulgite, montmorillonite or the like, in sufficient amount to provide from about 2% to 20% and preferably about 3% to 15% by weight, of active ingredient based on the total weight of the granulated product.

Wettable powder formulations are prepared by grinding together about 30% to 75% by weight of the active dibenzoyl-tert-butylcarbazonitrile with about 5% to 10% by weight of an anionic surfactant, such as a naphthalene sulfonate condensate or a sodium or ammonium salt of a condensed mono naphthalene sulfonic acid; about 3% to 5% by weight of an anionic surfactant such as an alkyl naphthalene sulfonate i.e. sodium di-n-butyl naphthalene sulfonate, sodium diisopropyl naphthalene sulfonate or the like and the remainder of the composition an inert diluent such as attapulgite, kaolin, montmorillonite, talc, diatomaceous earth or the like.

Process of Manufacture

The formula (I) and formula (II) dibenzoyl-tert-butylcarbazonitriles of this invention are prepared by reaction of a formula (III) substituted or unsubstituted dibenzoyl-tert-butylhydrazide with an alkali metal hydride, preferably sodium hydride and a cyanogen halide, preferably cyanogen bromide. The reaction is generally conducted in the presence of an inert organic solvent, preferably anhydrous tetrahydrofuran. The reactions are illustrated as follows:

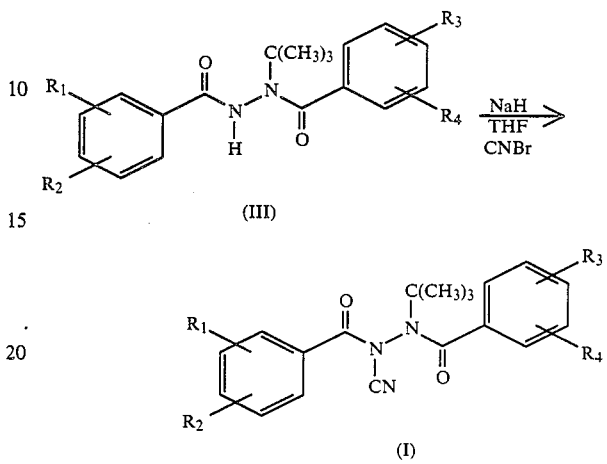

wherein $R_1$, $R_2$, $R_3$ and $R_4$ are each independently H, F, Cl, Br, I, $CH_3$, $OCH_3$, $OCF_3$, $CF_3$, $OCHF_2$, CN or $NO_2$.

The reaction is more preferably conducted in a two phase system in the presence of an inert organic solvent such as methylene chloride and aqueous alkali metal hydroxide, and a phase transfer catalyst such as tetrabutyl ammonium hydrogen sulfate or benzylmethyl ammonium chloride and the like, as illustrated below,

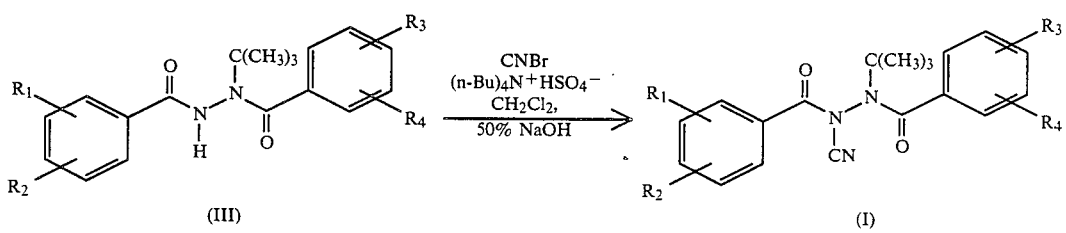

wherein $R_1$, $R_2$, $R_3$ and $R_4$ are as described hereinabove.

The formula (III) dibenzoyl-tert-butylhydrazides utilized in the above-described reaction are readily prepared by reaction of approximately equimolar amounts of a benzoic acid alkylhydrazide and a benzoyl halide in the presence of an aprotic solvent such as an ether, chlorinated hydrocarbon or the like and aqueous base. Generally, about two to six molar equivalents of base per equivalent of benzoic acid alkylhydrazide are sufficient to bring the reaction to completion. The reaction is graphically illustrated below,

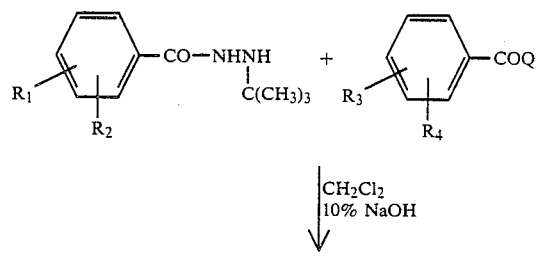

-continued

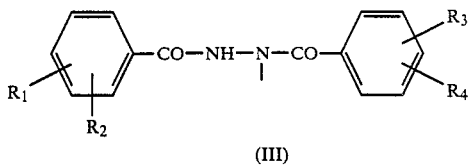

(III)

wherein $R_1$, $R_2$, $R_3$ and $R_4$ are as described and Q is halogen, preferably Cl or Br.

The benzoic acid alkylhydrazides utilized in the preparation of the formula (III) dibenzoyl-tert-butylhydrazides, also are prepared by dispersing a tert-butylhydrazine hydrohalide in an organic solvent, such as methylene chloride, ether or the like, and admixing the resulting mixture with an aqueous base.

Usually, about two to six molar equivalents of base, such as sodium carbonate or sodium hydroxide, per equivalent of tert-butylhydrazine hydrohalide are used to achieve the benzoylation of the tert-butylhydrazine. The thus-prepared mixture is then admixed with the appropriate benzoyl halide dissolved or dispersed in an organic solvent, preferably the same solvent used for dissolution of the tert-butylhydrazine hydrohalide.

The mixture is stirred or agitated for a sufficient period of time to form the benzoic acid tert-butylhydrazide which is readily recovered from the mixture by separation of the aqueous phase from the organic phase and evaporation of the organic solvent from said organic phase.

The reaction is graphically illustrated below,

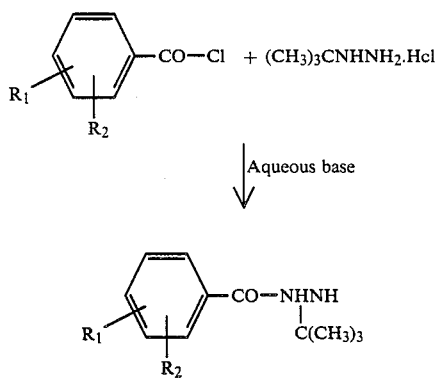

wherein $R_1$ and $R_2$ are as described.

The following examples are presented herein as illustrations of the present invention and are not intended to limit the invention.

EXAMPLE 1

Preparation of 2,3-dibenzoyl-2-tert-butylcarbazonitrile

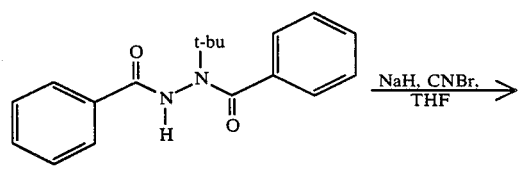

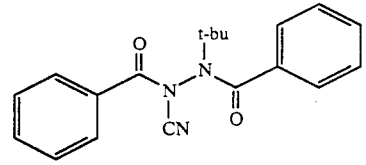

To a solution of dibenzoyl t-butylhydrazide (14.82 g, 0.05 mol) in anhydrous tetrahydrofuran (100 mL), sodium hydride (60% in oil, 2.40 g as is, 1.44 g real, 0.06 mol) is added in portions at room temperature. Temperature of the reaction rises to 37°–40° C. during the addition. After 15 minutes cyanogen bromide (6.35 g, 0.06 mol) in tetrahydrofuran (10 mL) is added slowly to the reaction slurry as the temperature rises to 42°. The reaction mixture is refluxed for 30 minutes and cooled to room temperature. More sodium hydride (60% in oil, 0.8 g as is, 0.02 mol) and cyanogen bromide (2.12 g, 0.02 mol) is added successively and the reaction mixture is refluxed for 90 minutes.

The solvent is removed on a rotary evaporator and the residue treated with water and extracted with ether. The organic extract is washed with water and saturated NaCl, and dried over (MgSO$_4$). Evaporation of the ether gives a solid which is purified by flash column chromatography on silica gel using 5% ethyl acetate in methylene chloride as eluent. Fractions corresponding to the less polar material are combined and evaporated to a solid residue. Crystallization from hexanes gives a white solid residue (13.7 g, 85.% yield): mp 114.5°–115° C.; IR (Nujol) 2240 (N-CN), 1740(CO)cm$^{-1}$; $^1$H NMR 1.70(s, 9H, t-Bu); $^{13}$C NMR (CDCl$_3$) 172.2, 166.5(CO), 110(CN), 27.8(CO); Mass spec 322(M+1).

Anal. Calcd for C$_{19}$H$_{19}$N$_3$O$_2$ (321.36): C, 71.01; H, 5.96; N, 13.07. Found: C, 70.98; H, 5.94; N, 13.05.

Following the above procedure, but substituting 1-benzoyl-1-tert-butyl-2-(o-chlorobenzoyl)hydrazine for dibenzoyl-tert-butylhydrazine gives 2-benzoyl-3-tert-butyl 3-(O-chlorobenzoyl)carbazonitrile having a melting point of 128°–130° C.

EXAMPLE 2

Preparation of 2,3-dibenzoyl-2-tert-butylcarbazonitrile

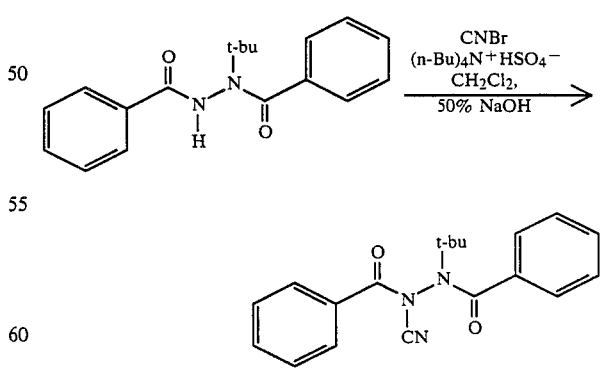

A solution of dibenzoyl-t-butylhydrazide (29.60 g, 0.1 mol) in methylene chloride (220 mL) is treated with tetra-n-butylammonium hydrogen sulfate (1.70 g, 0.005 mol, 5 mol%) using mechanical stirrer and a water bath. A solution of cyanogen bromide (15.90 g, 0.15 mol) in methylene chloride (40 mL) is prepared separately. To the reaction solution NaOH (50% aqueous, 52.3 mL, 40.00 g real, 1.0 mol) is added. The cyanogen bromide solution is then added to the reaction mixture over a 15-20 min period keeping the temperature of the reaction at 25°-28° C. by adding just enough ice to the water bath. The reaction is not allowed to cool below 20° C. or warm above 30° C. The reaction mixture is stirred for 20 minutes at 25°-27° C. A TLC of the reaction (silica gel, 2.5×10 cm, 5% ethyl acetate in methylene chloride) shows completion of the reaction and no starting material is observed.

The reaction mixture is diluted with ice-water. The organic layer is separated, washed well with water (2×200 mL) and saturated sodium chloride (100 mL), and dried ($Na_2SO_4$). Evaporation of the solvent leaves a solid residue which is dissolved in methylene chloride (50 mL) and hexanes (150 mL). On stirring the solution in an ice bath the product crystallizes. Additional hexanes (50 mL) is added to facilitate stirring and the solids are collected by filtration and dried (26.2 g, 83.5% yield): very pale yellow solid, mp 111.0°-111.5° C.; (recrystallized analytical sample from hexanes has mp 114.5°-115.0° C.; IR (Nujol) 2240 (N-CN), 1740, 1680 (CO) $cm^{01}$; $^1H$ NMR ($CDCl_3$) 1.70 d (s, 9H, t-Bu); $^{13}C$ NMR ($CDCl_3$) 172.3, 166.5 (CO), 110 (CN), 27.8 d (t-Bu).

EXAMPLE 3

Preparation of substituted dibenzoyl-tert-butylcarbazonitriles

Following the procedure of either example 1 or example 2 above, but substituting an appropriately substituted (as illustrated in example 4, table II below) formula (III) dibenzoyl-tert-butylhydrazide (as illustrated in example 4, Table II below) for dibenzoyl-tert-butylhydrazide, yields the substituted formula (I) dibenzoyl-tert-butylcarbazonitriles shown in Table I below.

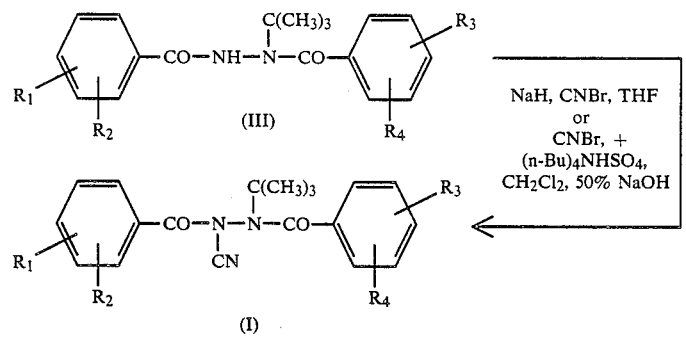

TABLE I

Formula (I)

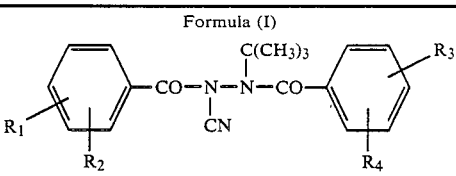

| $R_1$ | $R_2$ | $R_3$ | $R_4$ |
|---|---|---|---|
| H | 4Cl | H | 4Cl |
| 3Cl | 4Cl | 3Cl | 4Cl |
| 2CH₃ | H | 2CH₃ | H |
| 2Cl | 4Cl | 2Cl | 4Cl |
| H | 4CF₃ | H | 4CF₃ |
| H | 4OCH₃ | H | 4OCH₃ |
| 3C | 4Cl | H | H |
| 3Cl | 4Cl | H | 4Cl |
| 3Cl | 4Cl | H | 4CN |
| 3Cl | 4Cl | H | 4OCH₃ |
| 3Cl | 4Cl | 2CH₃ | H |
| 4Br | H | 4Br | H |
| H | 4F | H | 4F |
| 3Cl | 4Cl | H | 4NO₂ |
| 3Cl | 4Cl | H | 4CF₃ |
| 3Cl | 4Cl | H | 4CH₃ |
| H | H | 3Cl | 4Cl |
| 3Cl | 4Cl | 2F | 6F |
| H | 4CH₃ | H | 4CH₃ |
| H | 4Cl | 3Cl | 4Cl |
| 2F | H | 2F | H |
| 3Cl | 4Cl | 2CF₃ | H |
| 3Cl | H | 3Cl | H |
| H | 2Cl | H | 2Cl |
| 2F | 6F | 2F | 6F |
| 2Cl | 4NO₂ | 2Cl | 4NO₂ |
| 3Cl | 5Cl | 3Cl | 5Cl |
| H | 2CF₃ | H | 2CF₃ |
| H | 3CH₃ | H | 3CH₃ |
| 3Cl | 5Cl | 3Cl | 5Cl |
| 3Br | 4CH₃ | 3Br | 4CH₃ |
| 2I | H | 2I | H |
| 4I | H | 4I | H |
| 4NO₂ | H | 4NO₂ | H |
| 2Br | H | 2Br | H |
| 3F | H | 3F | H |
| 3F | 5F | 3F | 5F |
| 2F | 4F | 2F | 4F |
| 3Cl | 4Cl | 3CH₃ | 4Cl |
| H | H | H | 4Cl |
| H | 4Cl | H | 4CH₃ |
| H | H | H | 4CH₃ |
| 2Cl | H | H | 4F |
| H | H | 3Cl | H |
| H | H | 2Cl | H |
| 2Cl | H | H | H |
| 3Cl | H | H | H |
| H | 4Cl | H | H |
| 2Cl | H | 3Cl | H |
| 2Cl | H | 4Cl | H |
| 3Cl | H | 2Cl | H |
| H | 4Cl | 2Cl | H |
| H | 4Cl | H | 3Cl |
| 2NO₂ | H | H | H |
| H | 3Cl | H | 4Cl |
| H | H | H | 4F |
| H | 3F | H | 3Cl |
| H | H | 2NO₂ | H |
| 2NO₂ | H | H | 3Cl |

TABLE I-continued

Formula (I)

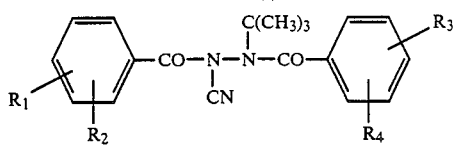

| R₁ | R₂ | R₃ | R₄ |
|---|---|---|---|
| H | 4F | H | H |
| 2F | H | H | H |
| H | H | 2F | H |
| H | H | 2OCH₃ | H |
| H | H | 2CH₃ | H |
| 2F | H | 2NO₂ | H |
| H | 4F | 2F | H |
| H | 4Cl | H | 4F |
| H | H | H | 3NO₂ |
| 2Cl | 4Cl | H | 4F |
| 2Cl | 4Cl | H | 3Cl |
| H | 4Cl | H | 4F |
| H | H | 2Br | H |
| H | H | H | 4Br |
| H | H | 2F | 6F |
| 2NO₂ | H | H | 4F |
| H | H | 2Cl | 4NO₂ |
| H | H | H | 4OCH₃ |
| H | H | 2I | H |
| H | H | H | 3OCH₃ |
| H | H | 2CN | H |
| H | H | 2CF₃ | H |
| H | H | 2Cl | 4Cl |
| H | H | 2OCH₃ | 6OCH₃ |
| H | H | 2F | 4Cl |
| 2F | 4Cl | 2F | 4Cl |
| 2I | H | H | H |
| H | H | 3F | H |
| H | H | 2NO₂ | 4Cl |

EXAMPLE 4

Preparation of 2-benzoyl-1-butyl-1-(3,4-dichlorobenzoyl)hydrazine

Benzoyl-2-tert-butylhydrazine (4.8 g, 0.025 mole) is stirred vigorously in a two-phase system of 50 mL of methylene chloride and 25 mL of 10% aqueous sodium hydroxide (2.5 g, 0.063 mol) until all dissolves. To this solution is added a solution of 3,4-dichlorobenzoyl chloride (7.3 g, 0.025 mol) in methylene chloride. After stirring the two-phase mixture several hours at ambient temperature, the solid is removed and washed with water and methylene chloride. Recrystallization from 2-propanol gives 7.1 g (78%) of product with mp 234°-235.5° C.

Following the procedure of this example, but substituting the appropriate benzoyl(alkyl)hydrazine for benzoyl-tert-butylhydrazine and the appropriate benzoyl halide for 3,4-dichlorobenzoyl halide, yields the compounds listed in Table II below. The reactions may be graphically illustrated as follows:

TABLE II

Compounds having the structure

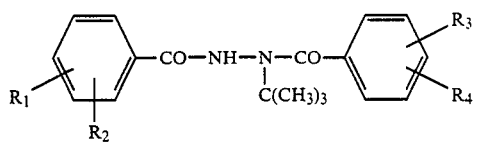

| R₁ | R₂ | R₃ | R₄ | mp °C. |
|---|---|---|---|---|
| H | 4Cl | H | 4Cl | >240 |
| 3Cl | 4Cl | 3Cl | 4Cl | 228.0–229.0 |
| 2CH₃ | H | 2CH₃ | H | 196.0–197.0 |
| 2Cl | 4Cl | 2Cl | 4Cl | 115.0–117.0 |
| H | 4CH₃ | H | 4CF₃ | 226.0–227.0 |
| H | 4OCH₃ | H | 4OCH₃ | 119.0–201.0 |
| 3Cl | 4Cl | H | H | 206.5–208.5 |
| 3Cl | 4Cl | H | 4Cl | >240 |
| 3Cl | 4Cl | H | 4CN | 230 |
| 3Cl | 4Cl | H | 4OCH₃ | >230 |
| 3Cl | 4Cl | 2CH₃ | H | 133.0–136.0 |
| 4Br | H | 4Br | H | 219.0–220.0 |
| H | 4F | H | 4F | 196.0–198.0 |
| 3Cl | 4Cl | H | 4NO₂ | >230 |
| 3Cl | 4Cl | H | 4CF₃ | 212.0–213.0 |
| 3Cl | 4Cl | H | 4CH₃ | 225.5–227.0 |
| H | H | 3Cl | 4Cl | 234.0–235.5 |
| 3Cl | 4Cl | 2F | 6F | 195.0–197.0 |
| H | 4CH₃ | H | 4CH₃ | 218.0–219.0 |
| H | 4Cl | 3Cl | 4Cl | 190.0–192.0 |
| 2F | H | 2F | H | 135.0–137.0 |
| 3Cl | 4Cl | 2CF₃ | H | 171.0–172.5 |
| 3Cl | H | 3Cl | H | 205.0–206.0 |
| H | 3Cl | H | 2Cl | 222.0–223.0 |
| 2F | 6F | 2F | 6F | 236.0 |
| 2Cl | 4NO₂ | 2Cl | 4NO₂ | 155.0–158.0 |
| 3Cl | 5Cl | 3Cl | 5Cl | 219.0–221.0 |
| H | 2CF₃ | H | 2CF₃ | 211.0 |
| H | 3CH₃ | H | 3CH₃ | 152.0–153.0 |
| 3Cl | 5Cl | 3Cl | 5Cl | 198.0–199.0 |
| 3Br | 4CH₃ | 3Br | 4CH₃ | 177.0–177.5 |
| 2I | H | 2I | H | 206.0–207.0 |
| 4I | H | 4I | H | >230.0 |
| 4NO₂ | H | 4NO₂ | H | >240.0 |
| 2Br | H | 2Br | H | 218.0–219.0 |
| 3F | H | 3F | H | 173.0–175.0 |
| 3F | 5F | 3F | 5F | 165.0–169.0 |
| 2F | 4F | 2F | 4F | 165.0–166.5 |
| 3Cl | 4Cl | 2CH₃ | 4Cl | 166.5–169.0 |
| H | H | H | 4Cl | 210.0–212.0 |
| H | 4Cl | H | 4CH₃ | 223.5–224.0 |
| H | H | H | 4CH₃ | 194.0–195.0 |
| 2Cl | H | H | 4F | >250 |
| H | H | 3Cl | H | 183.0–185.0 |
| H | H | 2Cl | H | 187.0–189.0 |
| 2Cl | H | H | H | 194.0–195.0 |
| 3Cl | H | H | H | 150.0–153.0 |
| H | 3Cl | H | H | 198.0–199.0 |
| 2Cl | H | 3Cl | H | 225.0–226.0 |
| 2Cl | H | 4Cl | H | 226.0–270.0 |
| 3Cl | H | 2Cl | H | 142.5–145.0 |
| H | 4Cl | 2Cl | H | 186.0–189.0 |
| H | 4Cl | H | 3Cl | 196.0–198.0 |
| H | 2NO₂ | H | H | H 213.0–216.0 |
| H | 3Cl | H | 4Cl | 233.5–234.0 |
| H | H | H | 4F | 212.0–213.0 |
| H | 3F | H | 3Cl | 206.0–207.0 |
| H | H | H | 2NO₂ | 165.0–172.0 |
| 2NO₂ | H | H | 3Cl | 200.0–203.0 |
| H | 4F | H | H | 196.0–198.0 |
| 2F | H | H | H | 152.0–155.0 |
| H | H | 2F | H | 175.0–177.0 |
| H | H | 2OCH₃ | H | 152.0–154.0 |
| H | H | 2CH₃ | H | 206.0–209.0 |
| 2F | H | 2NO₂ | H | 190.0–194.0 |
| H | 4F | 2F | H | 157.0–159.0 |
| H | 4Cl | H | 4F | 213.0–232.0 |
| H | H | H | 3NO₂ | 213.0–217.0 |
| 2Cl | 4Cl | H | 4F | 237.0–240.0 |
| 2Cl | 4Cl | H | 3Cl | 236.0–240.0 |
| H | 4Cl | H | 4F | 231.0–232.0 |
| H | H | 2Br | H | 184.0–187.0 |
| H | H | H | 4Br | 224.0–227.0 |
| H | H | 2F | 6F | 189.0–190.0 |

TABLE II-continued

Compounds having the structure

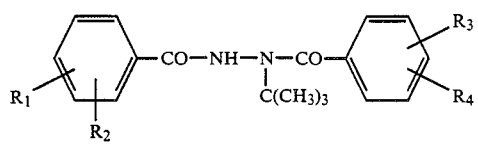

| R₁ | R₂ | R₃ | R₄ | mp °C. |
|---|---|---|---|---|
| 2NO₂ | H | H | 4F | 153.0–156.0 |
| H | H | 2Cl | 4NO₂ | 199.0–201.0 |
| H | H | H | 4OCH₃ | 217.0–218.0 |
| H | H | 2I | H | 175.0–177.0 |
| H | H | H | 3OCH₃ | — |
| H | H | 2CN | H | — |
| H | H | 2CF₃ | H | — |
| H | H | 2Cl | 4Cl | 136.0–138.0 |
| H | H | 2OCH₃ | 6OCH₃ | 175.0–176.0 |
| H | H | 2F | 4Cl | 154.0–155.0 |
| 2F | 4Cl | 2F | 4Cl | 105.0–106.0 |
| 2I | H | H | H | 223.0–224.0 |
| H | H | 3F | H | 173.0–174.0 |
| H | H | 2NO₂ | 4Cl | 129.0–131.0 |

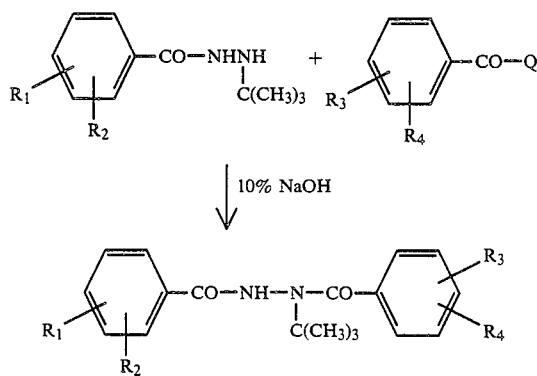

EXAMPLE 5

Insecticidal activity of the compounds of the invention

The insecticidal activity of the compounds of the present invention against a varoetu pf omsects at varoious concentrations of active ingredient in acetone-water solutions is determined by the following insecticidal test examples. The results of these tests are summarized in Table III.

*Spodoptera eridania*, third-instar larvae, southern armyworm

The leaves of a Sieva lima bean plant expanded to 7–8 cm in length are dipped in a test formulation with agitation for three seconds and placed in a hood to dry. A leaf is then excised and placed in a 100×10 mm petri dish containing a damp filter paper on the bottom and ten third-instar larvae. The dish is maintained for five days before observations are made of mortality, reduced feeding, or any interference with normal moulting.

*Spodoptera eridania*, seven-day residual

The plants treated in the above test are maintained under high intensity lamps in the greenhouse for seven days. These lamps duplicate the effects of a bright sunny day in June in New Jersey and are kept on for 14 hour day length. After seven days, the foliage is sampled and assayed as above.

*Heliothis virescens*, third-instar tobacco budworm

Cotton cotyledons are dipped in the solution of the test formulation and allowed to dry in a hood. When dry, each is cut into quarters and ten sections placed individually in 30 mL plastic medicine cups containing a 5–7 mm long piece of damp dental wick. One third-instar caterpillar is added to each cup and a cardboard lid placed on the cup. Treatments are maintained for three days at 27° C. before mortality counts and estimates of reduction in feeding damage are made.

Southern armyworm (*Spodoptera eridania*), third-instar, cut-stem systemic test

The compound is formulated as an emulsion containing 0.1 g of the test material, 0.1 g of a polyoxyethylated vegetable oil in 0.4 g water, 10 mL of acetone and 90 mL of water. This is diluted ten-fold with water to give the 100 ppm emulsion for the test. Sieva lima bean plants with just the primary leaves expanded are used in this test. The stem is cut off at least 2.5 cm above the soil level to avoid contamination with soil bacteria that will cause decay of the stem during the test.

The cut stems are placed in the test emulsions and each stem is wrapped with a bit of botton to hold the end off the bottom of the bottle and to limit evaporation. The test bottles are held for three days at 27° C. to enable the compound to be taken up into the leaf, keeping the room fluorescent lights on for 24 hours/day.

Following this, one leaf is removed from the plant and placed in 1 100×10 mm petri dish with ten southern armyworms. The petri dishes are held for five days at 27° C. before mortality counts and notations of feeding damage are taken.

*Empoasca abrupta*, Adults, Western Potato Leafhoppers, Systemic Uptake

The compound is formulated as an emulsion containing 0.1 gm of the test material, 0.2 gm of Emulphor El-620, emulsifier, 10 ml of acetone and 90 ml of water. This is diluted 10-fold with water to give a 100 ppm emulsion for the test. Subsequent 10-fold dilutions are made with water as needed. Sieva lima bean plants, with the primary leaves expanded to a length of 7–8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish and tested as in cut-stem systemic test described above for evaluation against the southern armyworm.

The rating system employed in these tests is as follows:

| Rating System | | |
|---|---|---|
| 0 | = | 0–10% kill |
| 1 | = | 11–25% kill |
| 2 | = | 26–35% kill |
| 3 | = | 36–45% kill |
| 4 | = | 46–55% kill |
| 5 | = | 56–65% kill |

-continued

| Rating System | | |
|---|---|---|
| 6 | = | 66–75% kill |
| 7 | = | 76–85% kill |
| 8 | = | 86–99% kill |
| 9 | = | 100% kill |

The absence of a number indicates that no test has been run at that particular dosage.

Where numbers are reported with a decimal, these numbers are an average of two or more tests.

Also, in the tobacco budworm (TBW-3) tests the numbers reported include a mortality rating and R value representing % reduced feeding.

Data obtained are reported in Table III.

TABLE III

Evaluation of test compounds as insecticidal agents having the structure:

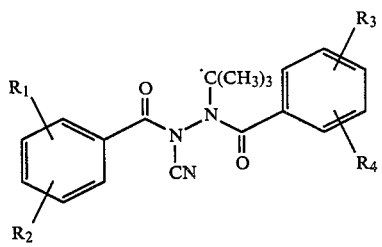

|  |  |  |  | Armyworms | | @7 Days | TBW-3 | | WPLH | | Cut-Stem Systemic | | | | | |
|---|---|---|---|---|---|---|---|---|---|---|---|---|---|---|---|---|
|  |  |  |  | | | | | | | | SAW | | WPLH | | SCRW | |
| $R_1$ | $R_2$ | $R_3$ | $R_4$ | 1000 (ppm) | 100 (ppm) | 1000 (ppm) | 1000 (ppm) | 100 (ppm) | 100 (ppm) | 10 (ppm) | 100 (ppm) | 10 (ppm) | 1 (ppm) | 100 (ppm) | 50 KG/HA | 10 KG/HA |
| H | H | H | H | 9 | 9 | — | 5.0 | 0, R7 | 9 | 0 | 9 | 9 | 3.5 | R8 | 9 | 0 |
| H | H | 2-Cl | H | 9 | 7.0 | 7.5 | 0, R7 | 0, R5 | 0 | — | 9 | 0 | — | 0 | 2.5 | 0 |

Armyworms = SAW = Southern armyworms
TBW-3 = Tobacco Budworms
SCRW = Southern Corn Rootworms
WPLH = Western Potato Leaf Hopper

What is claimed is:

1. A compound having the structural formula:

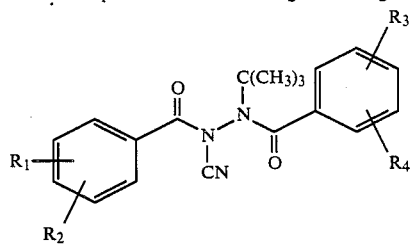

wherein $R_1$, $R_2$, $R_3$ and $R_4$ are each independently H, F, Cl, Br, I, $CH_3$, $OCH_3$, $OCF_3$, $CF_3$, $OCHF_2$, CN or $NO_2$.

2. A compound according to claim 1, wherein said compound is 2,3-dibenzoyl-2-tert-butylcarbazontrile.

3. A compound according to claim 1, wherein said compound is 2-benzoyl-3-tert-butyl 3-(o-chlorobenzoyl)carbazonitrile.

4. A method for protecting growing plants from insect attack, said method comprising: applying to the foliage of said plants or to the soil or water in which they are growing, a plant protecting, insecticidally effective, amount of a dibenzoyl-2-tert-butylcarbazonitrile having the structural formula, wherein $R_1$, $R_2$, $R_3$ and $R_4$ are each independently H, F, Cl, Br, I, $CH_3$, $OCH_3$, $OCF_3$, $CF_3$, $OCHF_2$, CN or $NO_2$.

5. A method according to claim 4 wherein said plants are agronomic crop plants, trees, shrubs, turf or ornamentals.

6. A method according to claim 5 wherein said dibenzoyl-2-tert-butylcarbazonitrile is applied to foliage of said plants and/or the soil or water in which they are growing at a rate of about 0.01 kg/hectare to 8.0 kg/hectare.

7. A method according to claim 6 wherein said dibenzoyl-2-tert-butylcarbazontrile is 2,3-dibenzoyl-2-tert-butylcarbazonitrile.

8. A method according to claim 6 wherein said dibenzoyl-2-tert-butylcarbazonitrile is 2-benzoyl3-tert-butyl 3-(o-chlorobenzoyl)carbazonitrile.

9. A method of systemically protecting a living plant through an extended period of active growth from insects which infest said growing plant, said method comprising: applying to the soil or other media in which it is growing, a systemically-effective amount of a compound having the formula,

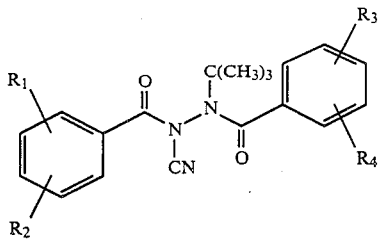

wherein $R_1$, $R_2$, $R_3$ and $R_4$ are each independentaly H, Cl, F, Br, I, $CH_3$, $OCH_3$, $CF_3$, $OCHF_2$, CN or $NO_2$.

10. A method according to claim 9, wherein said compound is 2,3-dibenzoyl-2-tert-butylcarbazonitrile.

11. A method according to claim 9, wherein said compound is 2-benzoyl-3-tert-butyl 3-(o-chlorobenzoyl)carbazontrile.

12. A method for the preparation of a dibenzoyl-tert-butylcarbazonitrile of formula (I) in a two phase system,

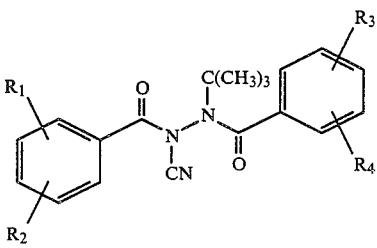

wherein $R_1$, $R_2$, $R_3$ and $R_4$ are each independently H, F, Cl, Br, I, $CH_3$, $OCH_3$, $OCH_3$, $CF_3$, $OCHF_2$, CN or $NO_2$, said method comprising: reacting a dibenzoyl-tert-butylhydrazide having the structure, (II)

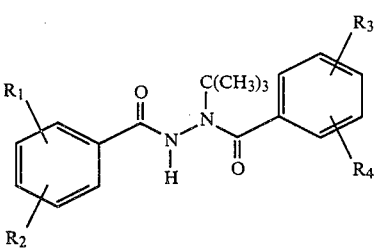

wherein $R_1$, $R_2$, $R_3$ and $R_4$ are as described, with a cyanogen halide in the presence of an inert organic solvent, an alkali metal hydroxide and a phase transfer catalyst selected from tetra-n-butylammonium hydrogen sulfate, and benzylmethylammonium chloride.

13. A method according to claim 12, wherein said cyanogen halide is cyanogen bromide, said solvent is methylene chloride, said base is sodium hydroxide, $R_1$, $R_2$ and $R_4$ are each hydrogen and $R_3$ is hydrogen or halogen.

14. A method for the preparation of a dibenzoyl-tert-butylcarbazonitrile of formula (I),

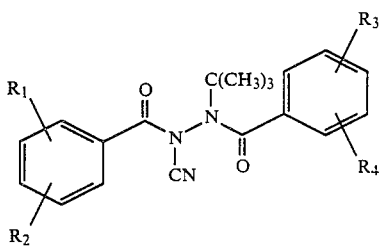

wherein $R_1$, $R_2$, $R_3$ and $R_4$ are each H, F, Cl, Br, I, $CH_3$, $OCH_3$, $OCF_3$, $CF_3$, $OCHF_2$, CN or $NO_2$, said mehtod comprising: reacting a dibenzoyl-tert-butylhydrazide having the structure, (II)

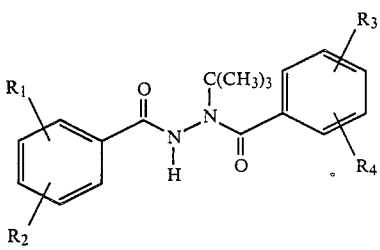

wherein $R_1$, $R_2$, $R_3$ and $R_4$ are as described, with an alkali metal hydride in the presence of an anhydrous ether; and thereafter treating the thus-formed reaction mixture with a cyanogen halide to obtain the desired dibenzoyl-tert-butylcarbazonitrile.

15. A method according to claim 14, wherein said alkali metal hydride is sodium hydride, said anhydrous ether is tetrahydrofuron, said cyanogen halide is cyanogen bromide, $R_1$, $R_2$ and $R_4$ are each hydrogen and $R_3$ is hydrogen or halogen.

* * * * *